(12) United States Patent
Peng et al.

(10) Patent No.: US 9,096,581 B2
(45) Date of Patent: Aug. 4, 2015

(54) FLUOROETHYL THIAMINE OR SALTS THEREOF AND APPLICATION THEREOF IN PREPARATION OF ANTICOCCIDIAL DRUGS

(71) Applicant: GUANGZHOU ORIGMOL FEED-ADDITIVE CO., LTD, Guangzhou, Guangdong (CN)

(72) Inventors: Xianfeng Peng, Guangzhou (CN); Zonghua Qin, Guangzhou (CN); Qijun Liu, Guangzhou (CN)

(73) Assignee: GUANGZHOU ORIGMOL FEED-ADDITIVE CO., LTD, Guangzhou (CN)

( * ) Notice: Subject to any disclaimer, the term of this patent is extended or adjusted under 35 U.S.C. 154(b) by 0 days.

(21) Appl. No.: 14/401,268

(22) PCT Filed: Mar. 15, 2013

(86) PCT No.: PCT/CN2013/072699
§ 371 (c)(1),
(2) Date: Nov. 14, 2014

(87) PCT Pub. No.: WO2013/170656
PCT Pub. Date: Nov. 21, 2013

(65) Prior Publication Data
US 2015/0133480 A1 May 14, 2015

(30) Foreign Application Priority Data
May 15, 2012 (CN) .......................... 2012 1 0151345

(51) Int. Cl.
| | | |
|---|---|---|
| A61K 31/51 | (2006.01) | |
| C07D 415/00 | (2006.01) | |
| C07D 417/06 | (2006.01) | |
| A23K 1/16 | (2006.01) | |

(52) U.S. Cl.
CPC ............ C07D 415/00 (2013.01); *A23K 1/1628* (2013.01); *A61K 31/51* (2013.01); *C07D 417/06* (2013.01)

(58) Field of Classification Search
CPC ..... A61K 1/1628; A61K 31/51; C07D 417/06
See application file for complete search history.

(56) References Cited

U.S. PATENT DOCUMENTS 3,786,147 A * 1/1974 Nagawa et al. ............... 514/256

FOREIGN PATENT DOCUMENTS

| CA | 1063617 A | * 10/1979 |
| CN | 102659776 A | 9/2012 |
| WO | WO 2013170656 A1 | * 11/2013 |

OTHER PUBLICATIONS

International Search Report in WO2013170656 (Feb. 2, 2015).*
S R. Al-Idreesi, 12 International Journal of Poultry Science, 157-163 (2013).*
Matsuzawa et al., "Anticoccidial Action of Thiamine Derivatives", Vitamins, vol. 42, No. 1, Jul. 25, 1970, pp. 22-26. Cited in ISR, previously submitted on Nov. 14, 2014.

* cited by examiner

*Primary Examiner* — Alexander R Pagano
(74) *Attorney, Agent, or Firm* — Westerman, Hattori, Daniels & Adrian, LLP

(57) ABSTRACT

The present invention discloses a fluoroethyl thiamine or salts thereof and application thereof in preparation of anticoccidial drugs. The structural formula of the fluoroethyl thiamine or salts thereof is shown as Formula (I). The fluoroethyl thiamine or salts thereof of the present invention have a remarkable anticoccidial effect, particularly on some coccidia which had resistance to other anticoccidial drugs, therefore the fluoroethyl thiamine or salts thereof of the present invention can be applied to preparation of anticoccidial drugs. Thus, the present invention provides conditions for development of new anticoccidial drugs.

Formula (I)

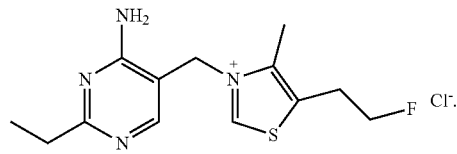

12 Claims, No Drawings

FLUOROETHYL THIAMINE OR SALTS THEREOF AND APPLICATION THEREOF IN PREPARATION OF ANTICOCCIDIAL DRUGS

FIELD OF THE INVENTION

The present invention relates to the field of biotechnology, and particularly to a fluoroethyl thiamine or salts thereof and application thereof in preparation of anticoccidial drugs.

BACKGROUND OF THE INVENTION

Coccidiosis caused by the protozoon of *Eimeria* spp is a significant animal epidemic disease which seriously harms the breeding production, wherein only chicken coccidiosis causes a loss of nearly 4 billion dollars in one year all over the world; the annual financial loss in breeding industry caused by the coccidiosis in China is up to nearly ten billion RMB. Apart from the chicken coccidiosis which exists for long and is widely known by people, in recent years, the morbidities of the swine coccidiosis, cow coccidiosis and the like are increasing year by year, and the swine coccidiosis has become a main disease cause of diarrhea and a death cause of piglets in lactation and weaning periods. *Eimeria tenella* is a direct life-cycle parasitic protozoon, which is difficult to kill due to its biological features. As long as there are intensive cultivations of pigs, chickens and so on, the infection of coccidium and the epidemic of coccidiosis cannot be avoided. Currently, the control on animal coccidiosis mainly depends on anticoccidial drugs, but the wide and long-time use of the anticoccidial drugs has resulted in universal generation of coccidium drug resistance, and particularly for chicken coccidium, the coccidium drug resistance in recent China's chicken industry has reached a very serious condition that almost no drug is effective. Therefore, the anticoccidial drugs are indispensable for controlling the animal coccidiosis forever, and new anticoccidial drugs are urgently needed in actual production.

SUMMARY OF THE INVENTION

The first purpose of the present invention aims at providing a new fluoroethyl thiamine or salts thereof, which have anticoccidial activity.

The fluoroethyl thiamine or salts thereof of the present invention have a structural formula as shown in Formula (I):

Formula (I)

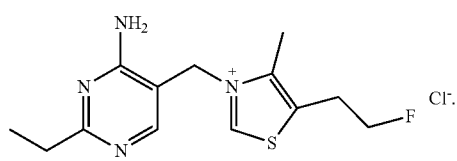

The fluoroethyl thiamine salts are preferably fluoroethyl thiamine hydrochlorides, and a structural formula thereof is as shown in Formula (II):

Formula (II)

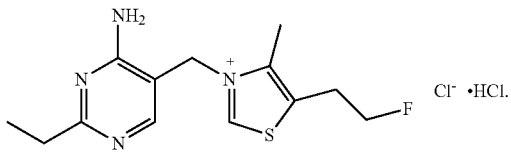

The second purpose of the present invention aims at providing application of the fluoroethyl thiamine or salts thereof as shown in Formula (I) in preparation of anticoccidial drugs.

The coccidium is preferably *eimeria tenella, eimeria acervulina, eimeria maxima* or *eimeria necatrix*.

The anticoccidial drugs are preferably anticoccidial drugs for poultry.

The poultry is preferably chicken.

The third purpose of the present invention aims at providing an anticoccidial drug, wherein, the anticoccidial drug comprises the fluoroethyl thiamine or salts thereof serving as an active ingredient.

The coccidium is preferably *eimeria tenella, eimeria acervulina, eimeria maxima* or *eimeria necatrix*.

The anticoccidial drugs are preferably anticoccidial drugs for poultry.

The poultry is preferably chicken.

The fluoroethyl thiamine or salts thereof of the present invention have a remarkable anticoccidial activity, particularly on some coccidia which have resistance to other anticoccidial drugs, therefore fluoroethyl thiamine or salts thereof can be applied to preparation of anticoccidial drugs. Thus, the present invention provides conditions for development of new anticoccidial drugs.

DETAILED DESCRIPTION OF THE EMBODIMENTS

The following embodiments are used for further describing rather than limiting the present invention.

I. Preparation of the Fluoroethyl Thiamine

Embodiment 1

(1) Synthesis of ethyl 4-amino-2-ethylpyrimidine-5-carboxylate

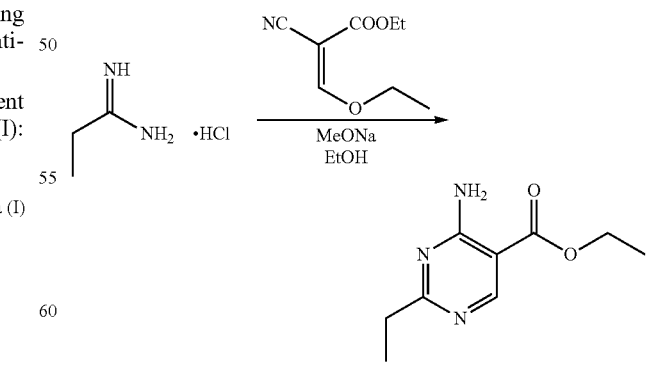

8.1 g (0.15 mol) of sodium methoxide was added to a dried single-neck flask equipped with constant pressure dropping funnel and drying pipe. The flask was cooled with ice bath for 10 min. 50 ml of absolute ethanol was added and the mixture was stirred. 10.857 g (0.1 mol) of propanimidamide monohydrochloride was charged into the flask after the sodium methoxide was dissolved, resulting a suspension. Then 16.9 g (0.1 mol) of ethyl cyano(ethoxymethylene)acetate in 70 ml of absolute ethanol was dropped into the flask through the dropping funnel. The reaction turned to yellow from white. The reaction was stirred for 1-2 h after the addition was finished. Ice water was poured into the flask. Precipitate formed was filtered and washed twice with water. 12 g of ethyl 4-amino-2-ethylpyrimidine-5-carboxylate was obtained (yield 62%) after drying.

$^1$H-NMR (400M, d-DMSO): 7.95 (s, 1H), 6.54 (s, 2H), 4.30 (dd, 2H, J=7.6, 14.8), 2.56 (dd, 2H, J=7.6, 15.2), 1.29 (t, 3H, J=7.6), 1.16 (t, 3H, J=7.6).

(2) Synthesis of 4-amino-2-ethyl-5-(hydroxymethyl)-pyrimidine

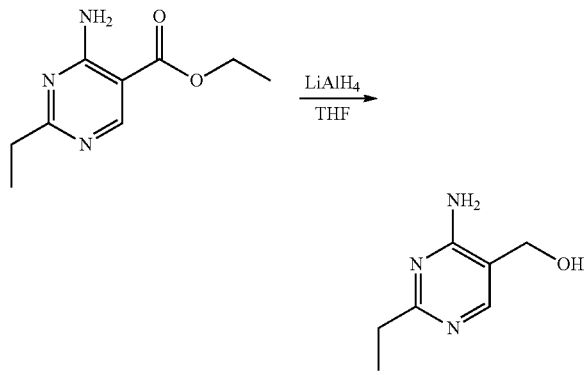

To a 100 ml flask equipped with constant pressure dropping funnel and drying pipe, 3.8 g (0.1 mol) of LiAlH$_4$ and 20 ml of THF were charged, cooled with ice bath. 7.8 g (0.04 mol) of 4-amino-2-ethylpyrimidine-5-carboxylate in the 20 ml of THF was dropped into the flask slowly. After the addition was finished, the reaction was stirred for 1-2 h. The reaction was quenched with water and the solid was removed by filtration. The filtrate was concentrated. To the residue, 20 ml of ethyl acetate and 120 ml of petroleum ether were added. After shaking and standing, large amount of white solids precipitated. 4.59 g of aim product was obtained by filtration (yield 75%).

$^1$H-NMR (400M, d-DMSO): 7.94 (s, 1H), 6.54 (s, 1H), 5.36 (s, 1H), 4.31 (s, 2H), 3.41 (s, 1H), 2.56 (dd, 2H, J=7.6, 15.2), 1.16 (t, 3H, J=7.6).

(3) Synthesis of 4-amino-5-chloromethyl-2-ethylpyrimidine hydrochloride

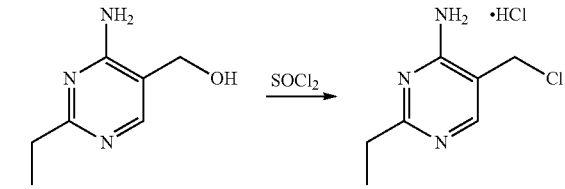

4.59 g (0.03 mol) of 4-amino-2-ethyl-5-(hydroxymethyl)-pyrimidine was charged into a 100 ml flask, followed by 20 ml of dichloromethane, 20 ml of toluene and 0.1 ml of pyridine. 6.5 ml of thionyl chloride (0.28 mol) was dropped in slowly with cooling by ice bath. Then the reaction was stirred overnight. Solvent was removed and the residue was used for next step directly.

$^1$H-NMR (400M, d-DMSO): 8.45 (s, 1H), 4.80 (s, 2H), 3.64 (s, 2H), 2.80 (dd, 2H, J=7.6, 14.8), 1.24 (t, 3H, J=7.6).

(4) Synthesis of 5-(2-fluoroethyl)-4-methylthiazole

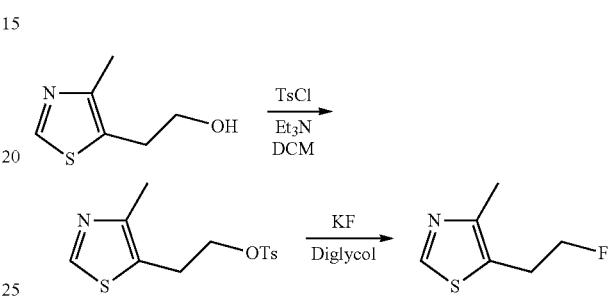

14.3 g (0.1 mol) of 4-methyl-5-(hydroxyethyl)-thiazole was charged into a 500 ml bottom-rounded flask, followed by 200 ml of dichloromethane and 28.65 g of TsCl (0.15 mol). To the flask 60.6 g of triethylamine was dropped into with cooling by ice bath. The reaction mixture was stirred for 2~3 h. 300 ml of dichloromethane was charged and the resulting solution was washed with water and water solution of sodium bicarbonate. To the organic phase 30 ml of dichloromethane and 200 ml of petroleum ether were charged. A precipitate was formed after shaking the mixture. It was filtered and transferred to 250 ml of flask. 150 ml of diglycol and 17.4 g of KF were added. The resulting mixture was stirred at 100° C. for 1 h and detected by TLC. 500 ml of water was added after the starting material disappeared. The reaction mixture was extracted by dichloromethane three times. The combined dichloromethane solution was washed with brine. Dichloromethane was removed under reduced pressure. 10.1 g of 5-(2-fluoroethyl)-4-methylthiazole was obtained by column chromatography (yield 70%).

1H-NMR (400M, d-CDCl3): 8.68 (s, 1H), 4.74 (t, 1H, J=5.6), 4.62 (t, 1H, J=5.6), 2.75 (t, 2H, J=5.6), 2.45 (s, 3H).

(5) Synthesis of 3-[(4-amino-2-ethyl-5-pyrimidyl)-methylene]-5-(2-fluoroethyl)-4-methyl thiazole chloride hydrochloride (fluoroethyl thiamine hydrochloride)

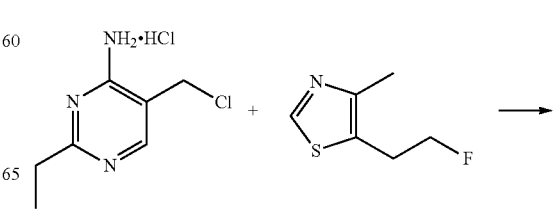

-continued

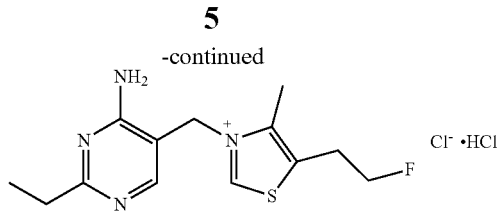

To 25 ml flask 1.7 g (8.2 mmol) of 4-amino-5-chloromethyl 2-ethylpyrimidine hydrochloride and 1.3 g (9.0 mmol) of 5-(2-fluoroethyl)-4-methylthiazole were charged, followed by 1 ml of DMSO. The reaction mixture was stirred at 100° C. for 20 minutes. Then it was cooled to room temperature and 10 ml of isopropanol was added. After standing for 2 h, a precipitate was formed and filtered. 2 g of 3-[(4-amino-2-methylpyrimidin-5-yl)methyl]-5-(2-fluoroethyl)-4-methylthiazol chloride hydrochloride was obtained as white solid (yield 70%).

$^1$H-NMR (400M, d-DMSO): 10.05 (s, 1H), 9.25 (s, 1H), 8.38 (s, 1H), 5.65 (s, 2H), 4.74 (t, 1H, J=5.6), 4.62 (t, 1H, J=5.6), 3.38 (t, 2H, J=5.6), 2.80 (t, 2H, J=7.6), 2.55 (s, 3H), 1.29 (t, 3H, J=7.6).

(6) Synthesis of chloride 3-[(4-amino-2-ethyl-5-pyrimidyl)-methylene]-5-(2-fluoroethyl)-4-methyl thiazole (fluoroethyl thiamine)

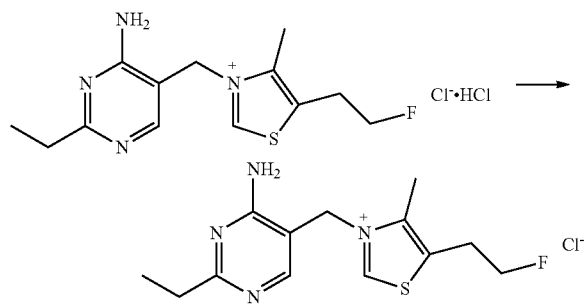

1 g of 3-[(4-amino-2-methylpyrimidin-5-yl)methyl]-5-(2-fluoroethyl)-4-methylthiazol chloride hydrochloride was dissolved in 50 absolute ethanol. 1 equivalent of 0.5 mol/L NaOH in water was added. The reaction mixture was stirred for 5 min at room temperature. Solvent was removed under reduced pressure. To the residue 10 ml of absolte ethanol was added and solid was filtered. To the filtrate 20 ml of diethyl ether was added. 0.85 g of 3-[(4-amino-2-ethyl-5-pyrimidyl)-methylene]-5-(2-fluoroethyl)-4-methyl thiazole chloride was obtained as crystal by filtration.

$^1$H-NMR (400M, d-DMSO): 10.00 (s, 1H), 9.21 (s, 1H), 8.35 (s, 1H), 5.61 (s, 2H), 4.73 (t, 1H, J=5.6), 4.60 (t, 1H, J=5.6), 3.34 (t, 2H, J=5.6), 2.76 (t, 2H, J=7.6), 2.50 (s, 3H), 1.29 (t, 3H, J=7.6).

II. Efficacy Experiments of the Fluoroethyl Thiamine:

Embodiment 2: Anticoccidial Dose Research of Fluoroethyl Thiamine Hydrochloride

1. Experiment Materials
1.1 Experiment Animals and Feed
1-day-old Lingnan yellow chickens, purchased from Poultry Research Unit, Bureau of Animal Husbandry, Guangdong Academy of Agricultural Sciences, bred under coccidium-free environment, and subjected to experiment after no coccidium oocyst is found in feces through microscopic examination when the chickens are 14 days old. Perfect compound feed for chickens: prepared by Huizhou Yuantai Feed Co. Ltd., and containing no antibacterial or anticoccidial additive.

1.2 Experiment Drug
Fluoroethyl thiamine hydrochloride, synthesized according to the method in Embodiment 1.

1.3 Oocysts for Experiment
*Eimeria tenella* GD strains, having no resistance to various anticoccidial drugs. Breeding and amplifying in chickens before the experiment, collecting fresh oocysts, sporulating, and preserving at 4° C. for later use.

2. Experiment Design
2.1 Experiment Grouping
Weighing the 14-day-old experiment chickens one by one, rejecting emaciated or overweighted chickens, selecting healthy chickens of which the individual body weight difference is within 20 g, and dividing to 9 groups with 20 chickens in each group. Groups 1 and 2 are respectively a non-drug-applied and non-coccidium-killed control group and a coccidium-infected and non-drug-applied control group, and Groups 3-9 are experiment groups applied with different doses of the fluoroethyl thiamine hydrochloride according to Table 1. Adding different doses of drugs to feeds and mixing uniformly on the day of experiment grouping, enabling the chickens to freely take in the feeds, and feeding the chickens until the experiment ends.

TABLE 1 experiment animal grouping and drug usage

| group | number of experiment animals | drug | dose(ppm) |
|---|---|---|---|
| 1 | 20 | — | — |
| 2 | 20 | — | — |
| 3 | 20 | fluoroethyl thiamine hydrochloride | 10 |
| 4 | 20 | fluoroethyl thiamine hydrochloride | 25 |
| 5 | 20 | fluoroethyl thiamine hydrochloride | 50 |
| 6 | 20 | fluoroethyl thiamine hydrochloride | 75 |
| 7 | 20 | fluoroethyl thiamine hydrochloride | 100 |
| 8 | 20 | fluoroethyl thiamine hydrochloride | 150 |
| 9 | 20 | fluoroethyl thiamine hydrochloride | 200 |

2.2 Experiment Method
Except the non-coccidium-infected and non-drug-applied control group (Group 1), giving each experiment chicken in each experiment group with $2.5 \times 10^5$ *eimeria tenella* sporulated oocysts via the crop on the next day of the grouping day. During experiment, observing and recording the spirit, appetite, bloody feces situation, death count and the like of the chickens every day. Performing bloody feces scoring on the chickens in each group 5 days after infecting. On the $7^{th}$ day, respectively weighing all the chickens in each group, then autopsying them, observing cecum lesions and counting the oocysts in the cecum.

2.3 Anticoccidial Effect Evaluation
2.3.1 Bloody feces scoring: according to the method in the references: 0 point, no bloody feces, 1 point, less than 25% of bloody feces; 2 points, 25%-50% of bloody feces; 3 points, 50%-75% of bloody feces; 4 points, more than 75% of bloody feces.

2.3.2 Weight gain: respectively weighing each chicken when the experiment starts and ends, and calculating the average weight gain and relative weight gain rate. The relative weight gain rate=(the average weight gain in the experiment groups/the average weight gain in the non-infected and non-drug-applied control group)×100%.

2.3.3 Survival rate: recording the number of dead chickens of each group, autopsying to determine the death cause, and calculating the survival rate. The survival rate=(the total number of the chickens in the experiment groups−the number of the chickens dying of coccidium infection during the experiment)/the total number of the chickens in the experiment groups×100%.

2.3.4 Lesion standard: killing the chickens 7 days after infecting, performing cecum lesion scoring according to the lesion scoring of Johnson and Reid (1970), and converting lesion points to lesion values.

lesion scoring (taking the serious side if the two sides of the cecum are inconsistent in lesion): 0 point, no macroscopic lesion; 1 point, a small amount of scattered petechiae on the cecum wall, no incrassation on the cecum wall, normal contents; 2 points, a large amount of lesion, obviously bloody contents in the cecum, slight incrassation on the cecum wall, normal contents; 3 points, a large a mount of blood or intestinal core (blood clot or gray caseous banana-shaped lumps) in the cecum, obvious incrassation on the cecum wall, a small amount of feces in the cecum; 4 points, cecum swelling caused by filling of a large amount of blood or intestinal core with or without feces in the intestinal core. Recording the dead chicken lesion as 4 points as well.

Lesion value (0-40)=the average lesion point of each group (0-4)×10

2.3.5 Oocysts counting and oocyst value: scraping the cecum contents, digesting the cecum contents with 10% sodium hypochlorite for 15 min, counting through a blood counting chamber and converting the number of the oocysts in each part of ceca to oocyst value. The conversion relation is shown in Table 2.

2.3.6 Anticoccidial Index (ACI)
Calculating the anticoccidial index according to the following formula, namely:

ACI=(relative weight gain rate+survival rate)×100−(lesion value+oocyst value).

Criteria of the drug efficiency: high-efficiency anticoccidial drugs if ACI≥180; intermediate-efficiency anticoccidial drugs if 160≤ACI<180; low-efficiency anticoccidial drugs if 120≤ACI<160; ineffective for coccidia if ACI<120.

3. Experiment Results
The results of relative weight gain rate, survival rate, lesion value, oocyst value and ACI of each experiment group are listed in Table 3. Judging from the anticoccidial index, when adding 50 or 75 ppm fluoroethyl thiamine hydrochloride in the feed, the anticoccidial indexs are respectively 165.5 and 176.4, which can achieve the level of intermediate-efficiency anticoccidial drugs. While adding 100, 150 or 200 ppm fluoroethyl thiamine hydrochloride in the feeds the anticoccidial indexs are respectively 195.9, 201.4 and 200.8, which can achieve the level of high-efficiency anticoccidial drugs.

TABLE 3

Experiment results

| group | drug dose (ppm) | bloody feces scoring | survival rate (%) | average weight gain (g/chicken) | relative weight gain rate (%) | lesion value | number of oocysts in cecum (×10$^6$/chicken) | oocyst value | anticoccidial index (ACI) |
|---|---|---|---|---|---|---|---|---|---|
| 1 | 0 | 0 | 100 | 167.2 | 100 | 0 | 0 | 0 | 200 |
| 2 | 0 | 4 | 60 | 102.9 | 61.5 | 33.5 | 2.025 | 10 | 78.0 |
| 3 | 10 | 2 | 90 | 135.7 | 81.2 | 24.5 | 2.965 | 10 | 136.7 |
| 4 | 25 | 2 | 90 | 139.5 | 83.4 | 18.8 | 2.325 | 10 | 144.6 |
| 5 | 50 | 1 | 100 | 144.9 | 86.7 | 11.2 | 3.65 | 10 | 165.5 |
| 6 | 75 | 0 | 100 | 158.7 | 94.9 | 8.5 | 2.15 | 10 | 176.4 |
| 7 | 100 | 0 | 100 | 162.0 | 96.9 | 0 | 0.47 | 1 | 195.9 |
| 8 | 150 | 0 | 100 | 171.2 | 102.4 | 0 | 0.16 | 1 | 201.4 |
| 9 | 200 | 0 | 100 | 168.5 | 100.8 | 0 | 0 | 0 | 200.8 |

Embodiment 3: Comparison of Effects Between the Fluoroethyl Thiamine Hydrochloride and Other Anticoccidial Drugs 1. Experiment Materials
1.1 Experiment Animals and Feed
1-day-old Lingnan yellow chickens, purchased from Poultry Research Unit, Bureau of Animal Husbandry, Guangdong Academy of Agricultural Sciences, bred under coccidium-free environment, and subjected to experiment after no coccidium oocyst is found in feces through microscopic examination when the chickens are 14 days old. Perfect compound feed for chickens: prepared by Huizhou Yuantai Feed Co. Ltd., and containing no antibacterial or anticoccidial additive.

1.2 Experiment Drugs
Fluoroethyl thiamine hydrochloride, synthesized according to the method in Embodiment 1.

TABLE 2

The conversion relation between the number of oocysts and the oocyst value

The number of oocysts (N × 10$^6$)

| | N ≤ 0.1 | 0.1 < N ≤ 1 | 1 < N ≤ 2 | 2 ≤ N ≤ 5 | 5 < N < 6 | 6 ≤ N ≤ 10 | 10 < N ≤ 11 | N ≥ 11.0 |
|---|---|---|---|---|---|---|---|---|
| The oocyst value | 0 | 1 | 5 | 10 | 15 | 20 | 30 | 40 |

Amprolium, nicarbazin and maduramicin, purchased from SIGMA Company.

1.3 Oocysts for Experiment

*Eimeria tenella* GD strains, having no resistance to various anticoccidial drugs. Breeding and amplifying in one chicken before the experiment, collecting fresh oocysts, sporulating, and preserving at 4° C. for later use.

2. Experiment Design 2.1 Experiment Grouping

Weighing the 14-day-old experiment chickens one by one, rejecting emaciated chickens or overweighted chickens, selecting healthy chickens of which the individual body weight difference is within 20 g, and dividing into 6 groups with 30 chickens in each group. Groups 1 and 2 are respectively a non-drug-applied and non-coccidium-killed control group and a coccidium-infected and non-drug-applied control group, and Groups 3-6 are respectively added with different anticoccidial drugs according to Table 4. Feeding with feed containing different drugs on the day of experiment grouping, enabling the chickens to freely take in the feed, and feeding the chickens until the experiment ends.

TABLE 4 experiment animal grouping and drug usage

| group | number of experiment animals | drug | dose(ppm) |
|---|---|---|---|
| 1 | 30 | — | — |
| 2 | 30 | — | — |
| 3 | 30 | fluoroethyl thiamine hydrochloride | 125 |
| 4 | 30 | amprolium | 125 |
| 5 | 30 | nicarbazin | 125 |
| 6 | 30 | maduramicin | 5 |

2.2 Experiment Method

Except the non-coccidium-infected and non-drug-applied control group, giving each experiment chicken in each experiment group with $2.5 \times 10^5$ *eimeria tenella* sporulated oocysts via the crop on next day of the grouping day. During experiment, observing and recording the spirit, appetite, bloody feces situation, death count and the like of the chickens every day. Performing bloody feces scoring on the chickens in each group 5 days after infecting. On the $7^{th}$ day, respectively weighing all the chickens in each group, then autopsying them, observing cecum lesions and counting the oocysts in the cecum.

2.3 Anticoccidial Effect Evaluation

The evaluation standard is the same with Embodiment 2.

3. Experiment Results

The results of relative weight gain rate, survival rate, lesion value, oocyst value and ACI of each experiment group are listed in Table 5. Judging from the bloody feces scoring and anticoccidial index results, fluoroethyl thiamine hydrochloride, amprolium, nicarbazin and maduramicin are all high-efficiency anticoccidial drugs. When adding 125 ppm drugs in the feed, the anticoccidial indexes of these four drugs are respectively 201.6, 191.2, 192.9 and 186.7. But fluoroethyl thiamine hydrochloride is superior to amprolium and maduramicin in lesion and oocyst value, and superior to nicarbazin in weight gain.

TABLE 5 experiment results

| group | drug dose (ppm) | bloody feces scoring | survival rate (%) | average weight gain (g/chicken) | relative weight gain rate (%) | lesion value | number of oocysts in cecum ($\times 10^6$/chicken) | oocyst value | anticoccidial index (ACI) |
|---|---|---|---|---|---|---|---|---|---|
| 1 | 0 | 0 | 100 | 172.8 | 100 | 0 | 0 | 0 | 200 |
| 2 | 0 | 4 | 66.7 | 113.6 | 65.7 | 32.6 | 4.854 | 10 | 89.8 |
| 3 | fluoroethyl thiamine hydrochloride 125 | 0 | 100 | 175.6 | 101.6 | 0 | 0 | 0 | 201.6 |
| 4 | amprolium 125 | 0 | 100 | 166.3 | 96.2 | 4 | 0.566 | 1 | 191.2 |
| 5 | nicarbazin 125 | 0 | 100 | 160.5 | 92.9 | 0 | 0 | 0 | 192.9 |
| 6 | maduramicin 5 | 0 | 100 | 168.4 | 97.7 | 6 | 1.265 | 5 | 186.7 |

Embodiment 4: The Effects of the Fluoroethyl Thiamine Hydrochloride on Coccidium Drug-Resistant Strains 1. Experiment Materials 1.1 Experiment Animals and Feed 1-day-old Lingnan yellow chickens, purchased from Poultry Research Unit, Bureau of Animal Husbandry, Guangdong Academy of Agricultural Sciences, bred under coccidium-free environment, and subjected to grouping and experiment after no coccidium oocyst is found in feces through microscopic examination when the chickens are 14 days old.

Perfect compound feed for chickens: prepared by Huizhou Yuantai Feed Co. Ltd., and containing no antibacterial or anticoccidial additive.

1.2 Experiment Drugs

Fluoroethyl thiamine hydrochloride, synthesized according to the method in Embodiment 1.

Amprolium, purchased from SIGMA Company.

1.3 Oocysts for Experiment

*Eimeria tenella* JM strains, separated and purified from a chicken farm in Jiangmen, Guangdong, which are tested and identified to be amprolium-resistant coccidium strains. Breeding and amplifying in chickens before the experiment, collecting fresh eggs, sporulating, and preserving at 4° C. for later use.

2. Experiment Design 2.1 Experiment Grouping

Weighing the 14-day-old experiment chickens one by one, rejecting emaciated chickens or overweighted chickens, selecting healthy chickens of which the individual body weight difference is within 20 g, and dividing into 4 groups with 30 chickens in each group. Groups 1 and 2 are respectively a non-drug-applied and non-coccidium-killed control group and a coccidium-infected and non-drug-applied control group, and Groups 3 and 4 are respectively added with fluoroethyl thiamine hydrochloride and amprolium. Feeding with feed containing different drugs on the day of experiment grouping according to Table 6, enabling the chickens to freely take in the feed, and feeding the chickens until the experiment ends.

TABLE 6 experiment animal grouping and drug usage

| group | number of experiment animals | drug | dose(ppm) |
|---|---|---|---|
| 1 | 30 | — | — |
| 2 | 30 | — | — |
| 3 | 30 | fluoroethyl thiamine hydrochloride | 125 |
| 4 | 30 | amprolium | 125 |

2.2 Experiment Method

Except the non-coccidium-infected and non-drug-applied control group, giving each experiment chicken in each experiment group with $1.0 \times 10^5$ eimeria tenella sporulated oocysts via the crop on the next day of the grouping day. During experiment, observing and recording the spirit, appetite, bloody feces situation, death count and the like of the chickens every day. Performing bloody feces scoring on the chickens in each group 5 days after infecting. On the $7^{th}$ day, respectively weighing all the chickens in each group, then autopsying them, observing cecum lesions and counting the oocysts in the cecum.

2.3 Anticoccidial Effect Evaluation

The evaluation standard is the same with Embodiment 2.

3. Experiment Results

The results of relative weight gain rate, survival rate, lesion value, oocyst value and ACI of each experiment group are listed in Table 7. Judging from the bloody feces scoring and anticoccidial index results, *eimeria tenella* JM strain has resistance to amprolium, but fluoroethyl thiamine hydrochloride can protect the experiment chickens from being infected by the strains. And the result reflects that the fluoroethyl thiamine hydrochloride can overcome the resistance of coccidium to amprolium which has the similar structure with fluoroethyl thiamine hydrochloride.

Embodiment 5: The Anticoccidial Effects of the Fluoroethyl Thiamine Hydrochloride on *Eimeria acervulina*

1. Experiment Materials 1.1 Experiment Animals and Feed 1-day-old Lingnan yellow chickens, purchased from Poultry Research Unit, Bureau of Animal Husbandry, Guangdong Academy of Agricultural Sciences, bred under coccidium-free environment, and subjected to grouping and experiment after no coccidium oocyst is found in feces through microscopic examination when the chickens are 14 days old.

Perfect compound feed for chickens: prepared by Huizhou Yuantai Feed Co. Ltd., and containing no antibacterial or anticoccidial additive.

1.2 Experiment Drugs

Fluoroethyl thiamine hydrochloride, synthesized according to the method in Embodiment 1.

Amprolium, purchased from SIGMA Company.

1.3 Oocysts for Experiment

*Eimeria acervulina* HT, having no resistance to various anticoccidial drugs. Breeding and amplifying in chickens before the experiment, collecting fresh eggs, sporulating, and preserving at 4° C. for later use.

2. Experiment Design 2.1 Experiment Grouping

Weighing the 14-day-old experiment chickens one by one, rejecting emaciated chickens or overweighted chicks, selecting healthy chickens of which the individual body weight difference is within 20 g, and dividing to 4 groups with 30 chickens in each group. Groups 1 and 2 are respectively a non-drug-applied and non-coccidium-killed control group and a coccidium-infected and non-drug-applied control group, and Groups 3 and 4 are added with fluoroethyl thiamine hydrochloride or amprolium according to Table 8. Feeding with feed containing different drugs on the day of experiment grouping, enabling the chickens to freely take in the feed, and feeding the chickens until the experiment ends.

TABLE 8 experiment animal grouping and drug usage

| group | number of experiment animals | drug | dose(ppm) |
|---|---|---|---|
| 1 | 30 | — | — |
| 2 | 30 | — | — |
| 3 | 30 | fluoroethyl thiamine hydrochloride | 125 |
| 4 | 30 | amprolium | 125 |

TABLE 7 experiment results

| group | drug dose (ppm) | bloody feces scoring | survival rate (%) | the average weight gain (g/chicken) | relative weight gain rate (%) | lesion value | number of oocysts in cecum ($\times 10^6$/chicken) | oocyst value | anticoccidial index (ACI) |
|---|---|---|---|---|---|---|---|---|---|
| 1 | 0 | 0 | 100 | 188.6 | 100 | 0 | 0 | 0 | 200 |
| 2 | 0 | 4 | 46.7 | 114.9 | 60.9 | 35.4 | 5.654 | 20 | 52.2 |
| 3 | amprolium 125 | 4 | 60 | 135.6 | 71.9 | 28.4 | 2.878 | 10 | 93.5 |
| 4 | fluoroethyl thiamine hydrochloride 125 | 0 | 100 | 182.7 | 96.8 | 0 | 0 | 0 | 196.8 |

2.2 Experiment Method

Except the non-coccidium-infected and non-drug-applied control group, giving each experiment chicken in each experiment group with $5\times10^5$ eimeria acervulina sporulated oocysts via the crop on the next day of the grouping day. During experiment, observing and recording the spirit, appetite, bloody feces situation, death count and the like of the chickens every day. On the $7^{th}$ day after infecting, respectively weighing each group, calculating the relative weight gain rate, simultaneously collecting feces samples, and counting the number of oocysts per gram of feces.

2.3 Anticoccidial Effect Evaluation 2.3.1 Weight gain: respectively weighing each chicken when the experiment starts and ends, and calculating the average weight gain and relative weight gain rate. The relative weight gain rate=(the average weight gain in the experiment groups/the average weight gain in the non-infected and non-drug-applied control group)×100%.

2.3.2 Survival rate: recording the number of dead chickens of each group, autopsying to determine the death cause, and calculating the survival rate. The survival rate=(the total number of the chickens in the experiment groups−the number of the chickens dying of coccidium infection during the experiment)/the total number of the chickens in the experiment groups×100%.

2.3.3 oocyst counting and relative decrement rate of oocysts: on the $7^{th}$ day after coccidium infection, digesting the collected fresh feces with 10% sodium hypochlorite for 15 min, counting the number of the coccidium oocysts per gram of feces through a blood counting chamber, and calculating the relative decrement rate of the oocysts in the feces of each experiment group. The relative decrement rate of oocysts= (the number of the oocysts per gram of feces in the coccidium-killed and non-drug-applied control group−the number of the oocysts per gram of feces in the experiment groups)/the number of the oocysts per gram of feces in the coccidium-killed and non-drug-applied control group×100%.

3. Experiment Results

The results of relative weight gain rate, survival rate, and oocyst decrement rate of each experiment group are listed in Table 9. Judging from the oocyst decrement results, fluoroethyl thiamine hydrochloride has a significant inhibition effect on the *eimeria acervulina*. When adding 125 ppm fluoroethyl thiamine hydrochloride in the feed, the fluoroethyl thiamine hydrochloride is superior to amprolium in *eimeria acervulina* inhibition.

Embodiment 6: The Anticoccidial Effects of the Fluoroethyl Thiamine Hydrochloride on *Eimeria maxima*

1. Experiment Materials 1.1 Experiment Animals and Feeds 1-day-old Lingnan yellow chickens, purchased from Poultry Research Unit, Bureau of Animal Husbandry, Guangdong Academy of Agricultural Sciences, bred under coccidium-free environment, and subjected to grouping and experiment after no coccidium oocyst is found in feces through microscopic examination when the chickens are 14 days old.

Perfect compound feed for chickens: prepared by Huizhou Yuantai Feed Co. Ltd., and containing no antibacterial or anticoccidial additive.

1.2 Experiment Drugs

Fluoroethyl thiamine hydrochloride, synthesized according to the method in Embodiment 1.

Amprolium, purchased from SIGMA Company.

1.3 Oocysts for Experiment

*Eimeria maxima* PY strains, having no resistance to various anticoccidial drugs. Breeding and amplifying in chickens before the experiment, collecting fresh oocysts, sporulating, and preserving at 4° C. for later use.

2. Experiment Design 2.1 Experiment Grouping

Weighing the 14-day-old experiment chickens one by one, rejecting emaciated chickens or overweighted chickens, selecting healthy chickens of which the individual body weight difference is within 20 g, and dividing to 4 groups with 30 chickens in each group. Groups 1 and 2 are respectively a non-drug-applied and non-coccidium-killed control group and a coccidium-infected and non-drug-applied control group, and Groups 3 and 4 are added with fluoroethyl thiamine hydrochloride or amprolium according to Table 10. Feeding with feed containing different drugs on the day of experiment grouping, enabling the chickens to freely take in feed, and feeding the chickens until the experiment ends.

TABLE 10 experiment animal grouping and drug usage

| group | number of experiment animals | drug | dose(ppm) |
|---|---|---|---|
| 1 | 30 | — | — |
| 2 | 30 | — | — |
| 3 | 30 | fluoroethyl thiamine hydrochloride | 125 |
| 4 | 30 | amprolium | 125 |

TABLE 9 experiment results

| group | drug | dose (ppm) | survival rate (%) | average weight gain (g) | relative weight gain rate (%) | number of oocysts in feces ($\times 10^4$/g) | relative decrement rate of oocysts (%) |
|---|---|---|---|---|---|---|---|
| 1 | — | — | 100 | 192.8 | 100 | 0 | 100 |
| 2 | — | — | 100 | 92.5 | 48.0 | 26.7 | — |
| 3 | fluoroethyl thiamine hydrochloride | 125 | 100 | 186.5 | 96.7 | 0.65 | 97.6 |
| 4 | amprolium | 125 | 100 | 166.6 | 86.4 | 2.98 | 88.8 |

2.2 Experiment Method

Except the non-coccidium-infected and non-drug-applied control group, giving each experiment chicken in each experiment group with 3×10⁵ *eimeria maxima* sporulated oocysts via the crop on the next day of the grouping day. During experiment, observing and recording the spirit, appetite, bloody feces situation, death count and the like of the chickens every day. On the 7$^{th}$ day after infecting, respectively weighing each group, calculating the relative weight gain rate, simultaneously collecting feces samples, and counting the number of oocysts per gram of feces.

2.3 Anticoccidial Effect Evaluation

The anticoccidial effect evaluation is the same with Embodiment 5.

3. Experiment Results

The results of relative weight gain rate, survival rate, and oocyst decrement results of each experiment group are listed in Table 11. Judging from the oocyst decrement results, fluoroethyl thiamine hydrochloride has a significant inhibition effect on *eimeria maxima*. When adding 125 ppm fluoroethyl thiamine hydrochloride in feed, the fluoroethyl thiamine hydrochloride is superior to amprolium in *eimeria maxima* inhibition.

weight difference is within 20 g, and dividing to 4 groups with 30 chickens in each group. Groups 1 and 2 are respectively a non-drug-applied and non-coccidium-killed control group and a coccidium-infected and non-drug-applied control group, and Groups 3 and 4 are added with fluoroethyl thiamine hydrochloride or amprolium according to Table 12. Feeding with feed containing different drugs on the day of experiment grouping, enabling the chickens to freely take in the feed, and feeding the chickens until the experiment ends.

TABLE 12 experiment animal grouping and drug usage

| group | number of experiment animals | drug | dose(ppm) |
|---|---|---|---|
| 1 | 30 | — | — |
| 2 | 30 | — | — |
| 3 | 30 | fluoroethyl thiamine hydrochloride | 125 |
| 4 | 30 | amprolium | 125 |

TABLE 11 experiment results

| group | drug | dose (ppm) | survival rate (%) | average weight gain (g) | relative weight gain rate (%) | number of oocysts in feces (×10⁴/g) | relative decrement rate of oocysts (%) |
|---|---|---|---|---|---|---|---|
| 1 | — | — | 100 | 179.9 | 100 | 0 | 100 |
| 2 | — | — | 100 | 123.2 | 68.5 | 4.20 | — |
| 3 | fluoroethyl thiamine hydrochloride | 125 | 100 | 176.3 | 98.0 | 0.37 | 91.2 |
| 4 | amprolium | 125 | 100 | 167.4 | 93.1 | 0.86 | 79.5 |

Embodiment 7: The Anticoccidial Effects of the Fluoroethyl Thiamine Hydrochloride on *Eimeria necatrix*

1. Experiment Materials 1.1 Experiment Animals and Feed 1-day-old Lingnan yellow chickens, purchased from Poultry Research Unit, Bureau of Animal Husbandry, Guangdong Academy of Agricultural Sciences, bred under coccidium-free environment, and subjected to grouping and experiment after no coccidium oocyst is found in feces through microscopic examination when the chickens are 14 days old.

Perfect compound feed for chickens: prepared by Huizhou Yuantai Feed Co. Ltd., and containing no antibacterial or anticoccidial additive.

1.2 Experiment Drugs

Fluoroethyl thiamine hydrochloride, synthesized according to the method in Embodiment 1.

Amprolium, purchased from SIGMA Company.

1.3 Oocysts for Experiment

*Eimeria necatrix* GD strains, having no resistance to various anticoccidial drugs. Breeding and amplifying in chickens before the experiment, collecting fresh oocysts, sporulating, and preserving at 4° C. for later use.

2. Experiment Design 2.1 Experiment Grouping

Weighing the 14-day-old experiment chickens one by one, rejecting emaciated chickens or overweighted chickens, selecting healthy chickens of which the individual body weight difference is within 20 g, and dividing to 4 groups with 30 chickens in each group.

2.2 Experiment Method

Except the non-coccidium-infected and non-drug-applied control group, giving each experiment chicken in each experiment group with 1×10⁵ *eimeria necatrix* sporulated oocysts via the crop on the next day of the grouping day. During experiment, observing and recording the spirit, appetite, bloody feces situation, death count and the like of the chickens every day. On the 7$^{th}$ day after infecting, respectively weighing each group, calculating the relative weight gain rate, simultaneously collecting feces samples, and counting the number of oocysts per gram of feces.

2.4 Anticoccidial Effect Evaluation

The anticoccidial effect evaluation is the same with Embodiment 5.

3. Experiment Results

The results of relative weight gain rate, survival rate, and in-feces oocyst decrement results of each experiment group are listed in Table 13. Judging from the weight gain and oocyst decrement results, fluoroethyl thiamine hydrochloride can effectively control infection of the *eimeria necatrix*. When adding 125 ppm fluoroethyl thiamine hydrochloride in feed, the fluoroethyl thiamine hydrochloride is superior to amprolium in *eimeria necatrix* inhibition.

TABLE 13

| | | | | | number | relative |
| | | | | relative | of | decrement |
| | | | average | weight | oocysts | rate of |
| | | survival | weight | gain | in feces | oocysts |
| group | drug | dose (ppm) | rate (%) | gain (g) | rate (%) | (×10⁴/g) | (%) |
|---|---|---|---|---|---|---|---|
| 1 | — | — | 100 | 185.6 | 100 | 0 | 100 |
| 2 | — | — | 63.3 | 88.4 | 47.6 | 1.35 | — |
| 3 | fluoroethyl thiamine hydrochloride | 125 | 100 | 172.5 | 92.9 | 0.19 | 85.9 |
| 4 | amprolium | 125 | 100 | 159.9 | 86.2 | 0.36 | 73.3 |

In conclusion, the fluoroethyl thiamine or salts thereof of the present invention have a remarkable anticoccidial effect, particularly on some coccidia which had resistance to other anticoccidial drugs, therefore the fluoroethyl thiamine or salts thereof of the present invention can be applied to preparation of anticoccidial drugs. Thus, the present invention provides conditions for development of new anticoccidial drugs.

The invention claimed is:

1. A fluoroethyl thiamine or salts thereof, having a structural formula as shown in Formula (I):

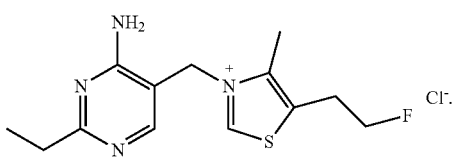

Formula (I)

2. The fluoroethyl thiamine or salts thereof according to claim 1, wherein the fluoroethyl thiamine salts are fluoroethyl thiamine hydrochlorides having a structural formula as shown in Formula (II):

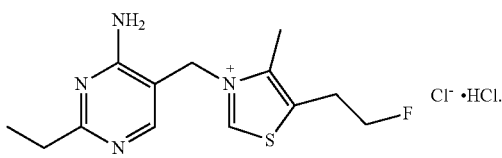

Formula (II)

3. An anticoccidial drug, comprising: the fluoroethyl thiamine or salts thereof of claim 1 as an active ingredient.

4. An anticoccidial drug, comprising:
the fluoroethyl thiamine or salts thereof of claim 2 as an active ingredient.

5. A method of treating coccidial infection, comprising:
administering a fluoroethyl thiamine or salts thereof having a structural formula as shown in Formula (I) to an animal

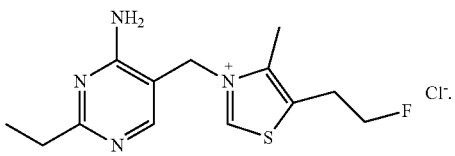

Formula (I)

6. The method of claim 5, wherein the coccidial infection is *eimeria tenella* infection, *eimeria acervulina* infection, *eimeria maxima* infection or *eimeria necatrix* infection.

7. The method of claim 5, wherein the animal is poultry.

8. The method of claim 5, wherein the animal is a chicken.

9. The method of claim 5, wherein the fluoroethyl thiamine salts are fluoroethyl thiamine hydrochlorides having a structural formula as shown in Formula (II):

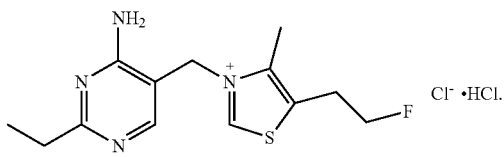

Formula (II)

10. The method of claim 9, wherein the coccidial infection is *eimeria tenella* infection, *eimeria acervulina* infection, *eimeria maxima* infection or *eimeria necatrix* infection.

11. The method of claim 9, wherein the animal is poultry.

12. The method of claim 9, wherein the animal is a chicken.

* * * * *